(12) United States Patent
Leimbach et al.

(10) Patent No.: US 8,864,681 B2
(45) Date of Patent: Oct. 21, 2014

(54) BIOPSY DEVICES

(75) Inventors: Jessica P. Leimbach, Cincinnati, OH (US); Edward A. Rhad, Fairfield, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 436 days.

(21) Appl. No.: 12/406,137

(22) Filed: Mar. 18, 2009

(65) Prior Publication Data
US 2009/0270760 A1     Oct. 29, 2009

Related U.S. Application Data

(60) Provisional application No. 61/047,160, filed on Apr. 23, 2008.

(51) Int. Cl.
| | | |
|---|---|---|
| *A61B 10/00* | (2006.01) | |
| *A61B 5/00* | (2006.01) | |
| *A61B 6/00* | (2006.01) | |
| *A61B 19/00* | (2006.01) | |
| *A61B 17/34* | (2006.01) | |
| *A61B 10/02* | (2006.01) | |

(52) U.S. Cl.
CPC ............ *A61B 19/54* (2013.01); *A61B 17/3403* (2013.01); *A61B 10/0275* (2013.01); *A61B 2019/5454* (2013.01); *A61B 2019/5404* (2013.01); *A61B 10/0283* (2013.01); *A61B 2017/3411* (2013.01); *A61B 2019/462* (2013.01); *A61B 2019/5408* (2013.01); *A61B 2019/542* (2013.01)
USPC ........... 600/567; 600/310; 600/436; 600/562; 600/564

(58) Field of Classification Search
CPC ........... A61B 10/0275; A61B 10/0283; A61B 19/54; A61B 17/3403; A61B 2019/5404; A61B 2019/5454

USPC ......... 600/309, 310, 312, 407, 436, 562, 564, 600/567; 606/167, 170, 184, 185; 604/27, 604/164.09, 164.11
See application file for complete search history.

(56) References Cited

U.S. PATENT DOCUMENTS

| | | | |
|---|---|---|---|
| 4,781,198 | A | 11/1988 | Kanabrocki |
| 5,526,822 | A | 6/1996 | Burbank et al. |

(Continued)

FOREIGN PATENT DOCUMENTS

| | | |
|---|---|---|
| EP | 1 897 507 | 3/2008 |
| EP | 2 113 204 | 11/2009 |

(Continued)

OTHER PUBLICATIONS

Partial European Search Report corresponding to European Patent Application No. 09251150.0 dated Jul. 7, 2009.

(Continued)

*Primary Examiner* — Sean Dougherty
*Assistant Examiner* — Devin Henson
(74) *Attorney, Agent, or Firm* — Frost Brown Todd LLC

(57) ABSTRACT

Biopsy devices and methods useful with Positron Emission Tomography (PET) and Breast Specific Gamma Imaging (BSGI) are disclosed. A biopsy device including a flexible tube having a side aperture, and a PET or BSGI imageable material disposed within the flexible tube is disclosed. A biopsy method is disclosed that includes advancing a flexible tube having a PET or BSGI imageable material distally through the biopsy device. Various other embodiments and applications are disclosed.

12 Claims, 15 Drawing Sheets

(56) References Cited

U.S. PATENT DOCUMENTS

| | | | |
|---|---|---|---|
| 5,647,374 A * | 7/1997 | Cutrer | 600/431 |
| 5,782,764 A * | 7/1998 | Werne | 600/411 |
| 5,938,604 A | 8/1999 | Wagner et al. | |
| 6,086,544 A | 7/2000 | Hibner et al. | |
| 6,228,055 B1 | 5/2001 | Foerster et al. | |
| 6,371,904 B1 | 4/2002 | Sirimanne et al. | |
| 6,471,700 B1 | 10/2002 | Burbank et al. | |
| 6,605,047 B2 * | 8/2003 | Zarins et al. | 600/562 |
| 6,993,375 B2 | 1/2006 | Burbank et al. | |
| 6,996,433 B2 * | 2/2006 | Burbank et al. | 600/431 |
| 7,044,957 B2 | 5/2006 | Foerster et al. | |
| 7,047,063 B2 | 5/2006 | Burbank et al. | |
| 7,083,576 B2 | 8/2006 | Zarins et al. | |
| 7,192,404 B2 | 3/2007 | Rhad et al. | |
| 7,229,417 B2 | 6/2007 | Foerster et al. | |
| 2003/0109801 A1 * | 6/2003 | Rhad et al. | 600/564 |
| 2003/0109803 A1 | 6/2003 | Huitema et al. | |
| 2004/0267121 A1 | 12/2004 | Sarvazyan et al. | |
| 2005/0027210 A1 | 2/2005 | Miller | |
| 2005/0228311 A1 | 10/2005 | Beckman et al. | |
| 2005/0261581 A1 | 11/2005 | Hughes et al. | |
| 2005/0277829 A1 | 12/2005 | Tsonton et al. | |
| 2005/0283069 A1 | 12/2005 | Hughes et al. | |
| 2006/0122503 A1 | 6/2006 | Burbank et al. | |
| 2006/0241385 A1 | 10/2006 | Dietz | |
| 2006/0258956 A1 | 11/2006 | Haberstich et al. | |
| 2007/0118048 A1 | 5/2007 | Stephens et al. | |
| 2007/0167736 A1 | 7/2007 | Dietz et al. | |
| 2007/0239067 A1 | 10/2007 | Hibner et al. | |
| 2007/0239103 A1 * | 10/2007 | Hardin et al. | 604/27 |
| 2007/0255168 A1 | 11/2007 | Hibner et al. | |
| 2007/0255170 A1 | 11/2007 | Hibner et al. | |
| 2007/0260267 A1 * | 11/2007 | Nicoson et al. | 606/130 |
| 2008/0015429 A1 | 1/2008 | Tsonton et al. | |
| 2008/0139928 A1 * | 6/2008 | Lubock et al. | 600/414 |
| 2008/0146962 A1 | 6/2008 | Ritchie et al. | |
| 2008/0195066 A1 | 8/2008 | Speeg et al. | |
| 2008/0200836 A1 | 8/2008 | Speeg et al. | |
| 2008/0214955 A1 | 9/2008 | Speeg et al. | |
| 2008/0221480 A1 | 9/2008 | Hibner et al. | |
| 2008/0228103 A1 | 9/2008 | Ritchie | |
| 2009/0163870 A1 * | 6/2009 | Flagle et al. | 604/164.01 |

FOREIGN PATENT DOCUMENTS

| | | |
|---|---|---|
| JP | H06-508782 | 10/1994 |
| JP | 2004-523283 | 8/2004 |
| JP | 2007-536063 | 12/2007 |
| JP | 2008-068065 A | 3/2008 |
| JP | 2008-547023 | 12/2008 |
| WO | WO 93/00859 | 1/1993 |
| WO | WO 98/22022 A1 | 5/1998 |
| WO | WO 02/60312 | 8/2002 |
| WO | WO 2005/110255 | 11/2005 |
| WO | WO 2007/002060 | 1/2007 |

OTHER PUBLICATIONS

Extended European Search Report Communication corresponding to European Patent Application No. 09251150.0 dated Oct. 13, 2009.

Extended European Search Report dated Jun. 14, 2010 for Application No. EP10250503.

Extended European Search Report dated Jun. 11, 2010 for Application No. EP10250504.

Extended European Search Report dated Jun. 14, 2010 for Application No. EP10250505.

European Search Report dated Apr. 10, 2012 for Application No. 10250504.7.

Japanese Office Action dated Jul. 28, 2014 for Application No. JP 2010-060258.

* cited by examiner

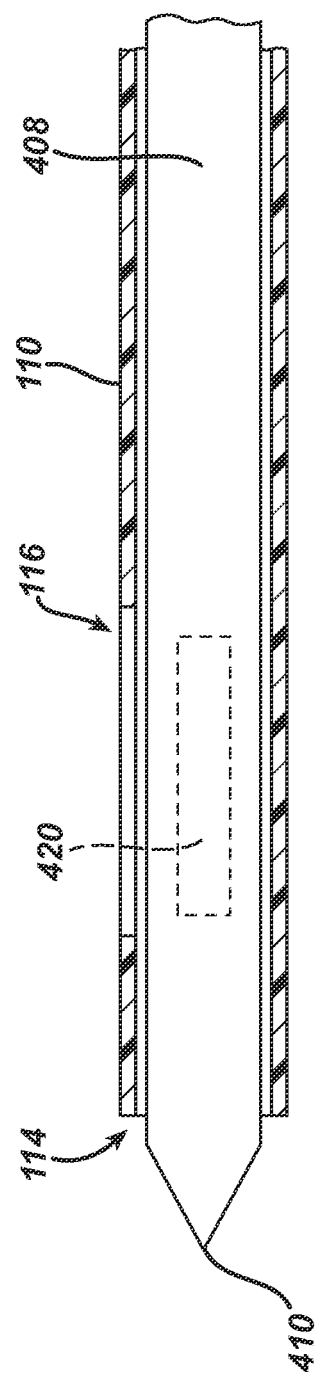

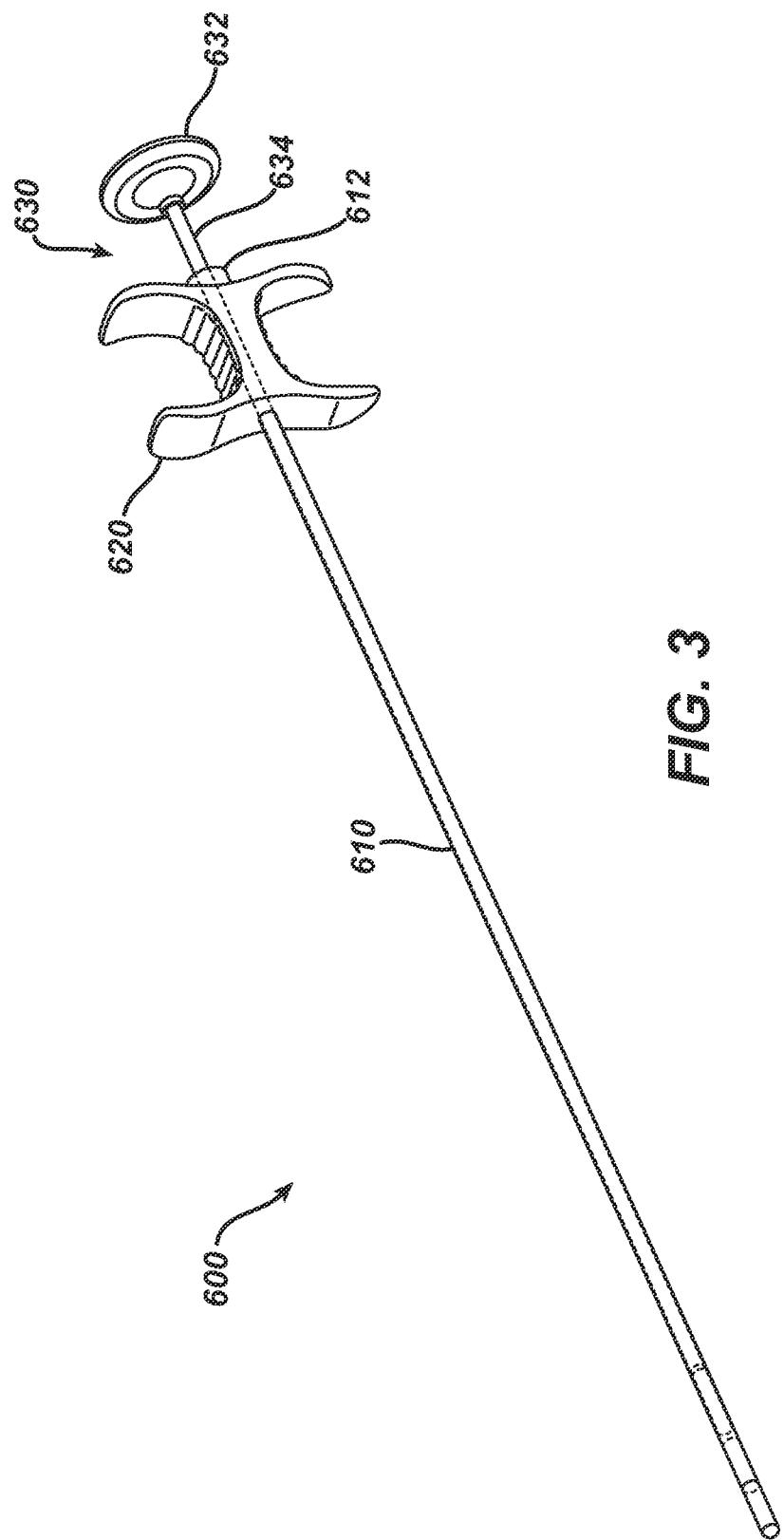

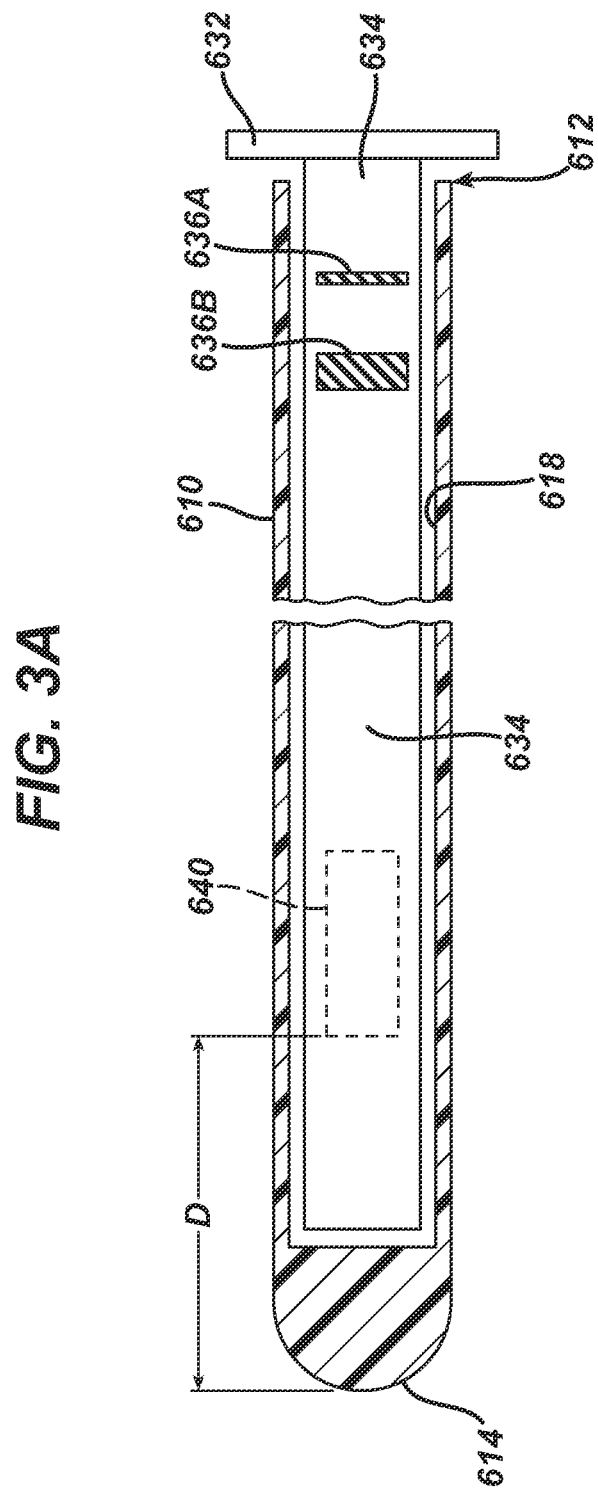

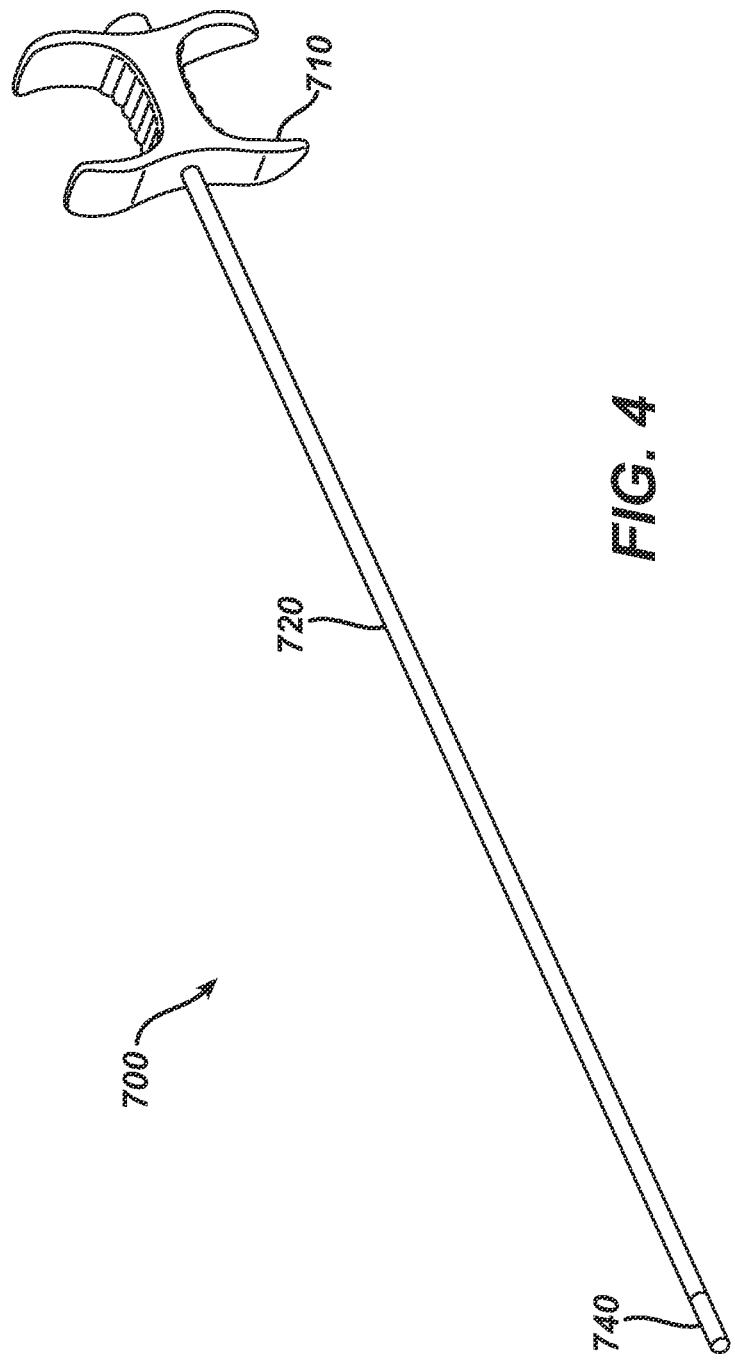

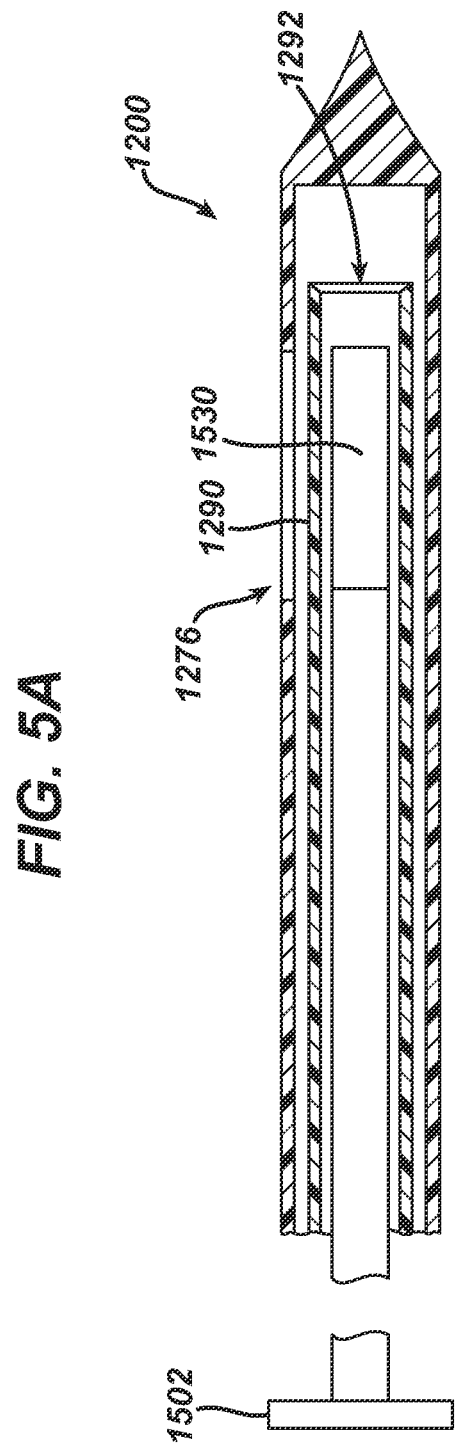

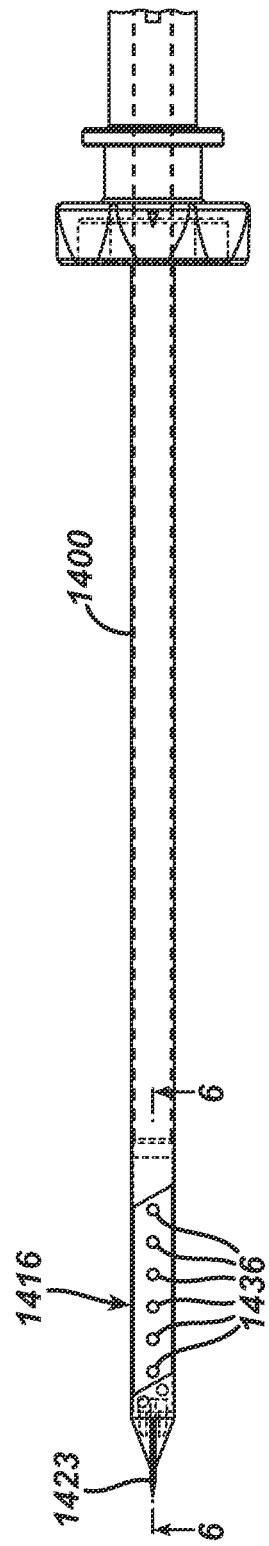
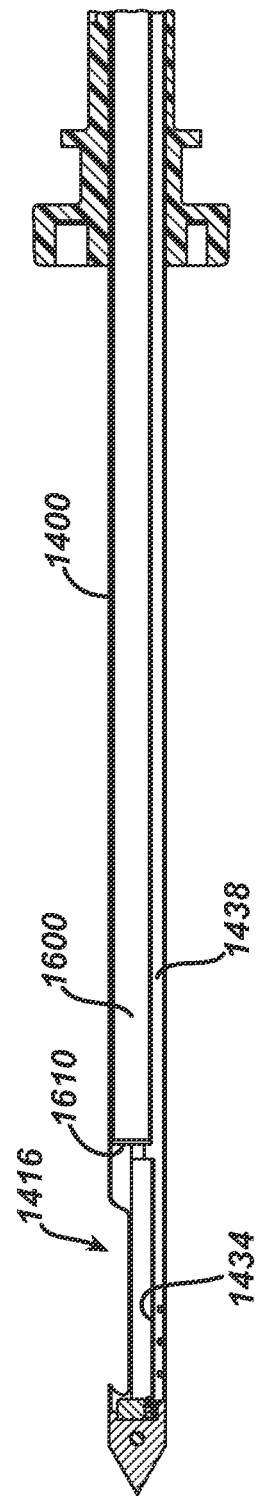
FIG. 6A
FIG. 6B

BIOPSY DEVICES

This application claims priority to U.S. Provisional Application 61/047,160 filed Apr. 23, 2008.

BACKGROUND

Biopsy samples have been obtained in a variety of ways using various devices. An exemplary biopsy device is the MAMMOTOME device from Ethicon Endo-Surgery, Inc. of Cincinnati, Ohio. Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. patents, U.S. Patent Application Publications, U.S. Provisional Patent Applications, and U.S. Non-Provisional patent application is incorporated by reference herein. While many of the foregoing biopsy devices are configured to obtain biopsy samples from breast tissue, biopsy samples may also be obtained from various other locations.

Various biopsy devices may be designed to work with X-ray, ultrasound, and magnetic resonance imaging (MRI) as imaging modalities. For instance, various components for interfacing biopsy devices with various imaging systems are disclosed in the following: U.S. Pub. No. 2005/0261581, entitled "MRI Biopsy Device," published Nov. 24, 2005; U.S. Pub. No. 2005/0277829, entitled "MRI Biopsy Apparatus Incorporating a Sleeve and a Multi-Function Obturator," published Dec. 15, 2005; U.S. Pub. No. 2005/0283069, entitled "MRI Biopsy Device Localization Fixture," published Dec. 22, 2005; U.S. Pub. No. 2007/0167736, entitled "MRI Biopsy Apparatus Incorporating an Imageable Penetrating Portion," published Jul. 19, 2007; U.S. Pub. No. 2006/0241385, entitled "Guided Disposable Fiducial for Breast Biopsy Localization Fixture," published Oct. 26, 2006; U.S. Pub. No. 2006/0258956, entitled "MRI Biopsy Device," published Nov. 16, 2006; U.S. Pub. No. 2007/0255168, entitled "Grid and Rotatable Cube Guide Localization Fixture for Biopsy Device," published Nov. 2, 2007; and U.S. Pub. No. 2007/0255170, entitled "Biopsy Cannula Adjustable Depth Stop," published Nov. 1, 2007; and US Pub No. 2008/0015429, "MRI Biopsy Device" published Jan. 17, 2008. The disclosure of each of the foregoing published patent applications is incorporated by reference herein.

It may be desirable in some settings to use one or more imaging modalities other than X-ray, ultrasound, or MRI before, during, or after a biopsy procedure. For instance, an alternative imaging modality may include positron emission tomography (PET) imaging. In a mammography context, such imaging may be referred to as positron emission mammography (PEM). Instead of scanning the entire body, PEM may be used as a special form of PET for imaging breasts and other small body parts. This may allow for a more detailed image of abnormal tissue. In a PEM context, the patient may be injected with an intravenous substance called FDG (fluorodeoxyglucose), which is a glucose analog, which may accumulate in glucose avid cells. This substance may carry a positron emitting radioactive isotope. One or more detectors may be used to capture emission of positrons emitted by such an isotope (e.g., by capturing resulting gamma photons) to ultimately produce an image. Alternatively, any other substances may be injected into a patient, as a tracing agent for PEM imaging or otherwise. An exemplary PEM system may include the PEM FLEX SOLO II system by Naviscan PET Systems, Inc. of San Diego, Calif.

Another alternative imaging modality may include breast-specific gamma imaging (BSGI). In a use of BSGI, a patient may be injected with a radiotracer (e.g., Technicium isotope T-99), and a BSGI camera may be used to capture gamma radiation emitted by such a tracer. Cancerous cells may have a higher tendency to absorb certain gamma emitting radiotracers, which may result in cancerous lesions standing out under BSGI imaging. BSGI imaging may thus provide distinction between cancerous tissue and non-cancerous tissue based on cellular activity rather than being based on tissue density. An exemplary BSGI system may include the DILON 6800 by Dilon Technologies of Newport News, Va.

Various biopsy site marker devices are disclosed for use in marking biopsy sites. One or more marker devices are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. patents and U.S. Patent Application Publications is incorporated by reference herein.

SUMMARY OF THE INVENTION

The use of a biopsy device with PEM and/or BSGI may warrant features or techniques that are different from those used with other imaging modalities. For instance, with X-ray it may be desirable to have a radiopaque biopsy needle to be able to determine if the needle is in the correct location in the target tissue. To target in ultrasound, it may be desirable for a biopsy probe needle has to have a good amount of echogenecity to be visible in the modality. With MRI, the ability to see the biopsy needle in the breast may mean that there should be no artifact in the needle to affect the targeted tissue area.

In a PEM and/or BSGI context, it may be desirable to incorporate an isotope (e.g., FDG isotope, isotope T-99, etc.) into at least a portion of targeting device and/or a biopsy device used to obtain a tissue sample. The presence of such an isotope in the biopsy device may permit or facilitate targeting in tissue, such as by facilitating verification that a targeted lesion has been reached. Such an isotope may be incorporated in a variety of biopsy device or system components, including but not limited to a portion of a biopsy needle, an obturator, or various portions of a targeting set, as will be described in greater detail below.

The present invention provides devices and methods useful in biopsy procedures associated with imaging methods employing isotopes.

In one embodiment, the invention provides a biopsy apparatus comprising a hollow, relatively flexible tube having an open proximal end; an elongate member advanceable in the tube; and at least one isotope disposed within the tube. The isotope may be carried by the elongate member, and the isotope may be disposed at a predetermined distance from a distal end of the tube. The tub may be non-metallic and have a closed distal end. The isotope may be positionable at a plurality of positions along the length of the tube, such as to accommodate biopsy apparatus having different sizes and/or shapes.

In another embodiment, the biopsy device comprises an outer biopsy needle having a tissue piercing distal tip, a side tissue receiving opening; a hollow inner cutter translatable within at least a portion of the needle, the cutter having a distal cutting edge for severing tissue received in the side tissue receiving opening; and an isotope disposed on a portion of one of the cutter and the biopsy needle.

The isotope may be disposed within the needle, such that the cutter may be advanced within the needle to separate, or at least partially separate, the isotope from tissue when the needle is advanced into tissue. In one embodiment, the isotope is disposed within the needle below the side tissue receiving opening.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 1A depicts the relatively rigid member of FIG. 1 positioned in the sleeve such that an isotope portion (shown in phantom) is aligned with a side aperture in the sleeve.

FIG. 3 depicts a perspective view of an introducer useful for positioning an isotope portion in or through a biopsy device, the introducer including a relatively flexible hollow tube such as the type used in flexible biopsy marker applications, and a relatively flexible elongate member slidably insertable in the flexible hollow tube, with the elongate member being sized and shaped to position the isotope portion at a predetermined distance along the flexible hollow member's length;

FIG. 3A illustrates the elongate member positioned in the hollow tube, with the isotope portion shown in phantom and spaced a predetermined distance D from a closed, distal end of the hollow tube.

FIG. 4 depicts a perspective view of another embodiment of an introducer having a generally flexible shaft with an isotope portion disposed at a distal end thereof, such as by attaching the isotope portion to the distal end of the flexible shaft, or by inbedding or molding the isotope portion in a distal end portion of the shaft;

FIG. 5A illustrates a hollow cutter advanced with a biopsy needle to close off a side tissue opening in the needle, and an isotope advanced into the cutter and aligned with the side tissue opening.

FIG. 6A depicts a top plan view of an exemplary biopsy needle incorporating an isotope;

FIG. 6B depicts a lateral side cross-section of the biopsy needle of FIG. 6A showing a hollow cutter disposed within the biopsy needle and an isotope associated with a portion of the needle located below a side tissue receiving aperture in the needle.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
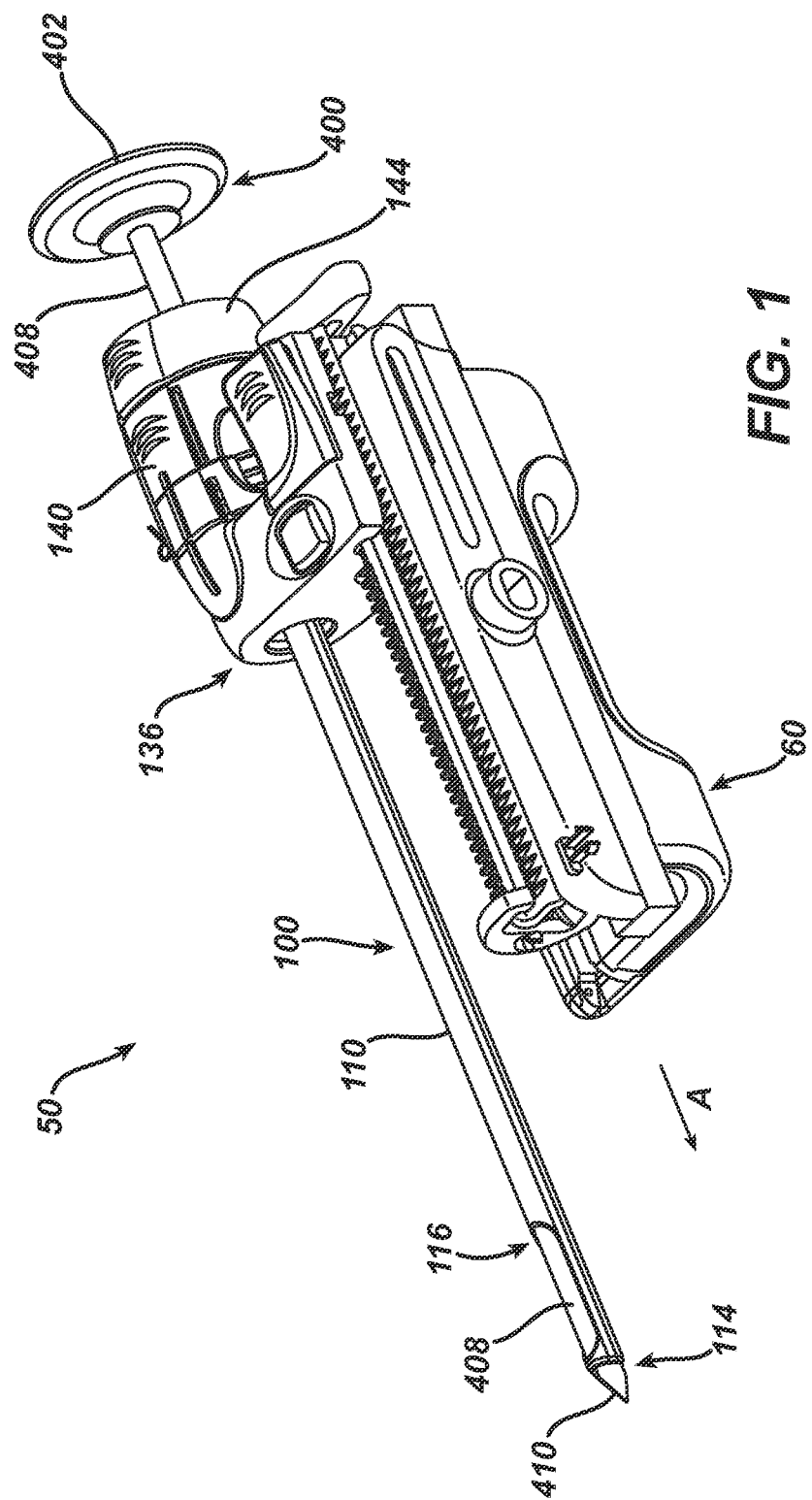
FIG. 1 depicts a perspective view of an exemplary biopsy targeting assembly illustrating an isotope introducer comprising a relatively rigid member, such as an obturator rod, inserted into a sleeve having an open distal end and a side aperture, with the relatively rigid rod having an isotope portion generally aligned with the side aperture in the sleeve when the relatively rigid member is inserted into the sleeve.

FIGS. 1 and 1A depict one biopsy targeting assembly 50 in accordance with the present invention that may be used with PEM, PET, BSGI, or other nuclear imaging systems utilizing an isotope or other radiation emitting source. The assembly shown can include similar structures employed in a targeting assembly described in one of published U.S. patent applications as being used in an MRI setting, such as US 2007/0255168 and US 2008/0015429 incorporated by reference herein. In addition, the targeting assembly 50 of the present example shown in FIG. 1 land FIG. 1A further includes an introducer 400 comprising an isotope, such as an isotope portion 420 (shown in Phantom in FIG. 2) visible under one or both of PET, PEM, and/or BSGI, and/or any other nuclear based imaging system where an isotope is used to verify target location.

Referring to FIGS. 1 and 1A, the targeting assembly 50 can include a sleeve assembly 100 supported by a sleeve mount 136. The assembly 50 can also include a cradle assembly 60. Cradle assembly 60 may provide support for a biopsy device having an outer biopsy needle and an inner cutter. Assembly 60 may also support the sleeve mount 136, such as for motion along a direction into which the biopsy instrument needle and the sleeve 110 is to directed into tissue (z direction) indicated by arrow A in FIG. 1. Sleeve assembly 100 may include an enlarged distal end portion 140 which may releasably latch to sleeve mount 136. The end portion 140 may include one or more internal seals for providing sealing around the elongate member 408 when the member 408 is inserted into the sleeve assembly 100. The assembly may also include a cap 144 which may include a through bore for receiving member 408, or alternatively cap 144 may cover an opening in end portion 140 when the introducer 400 is removed from the sleeve 110.

In the embodiment shown, the sleeve assembly 100 comprises a sleeve 110 having an open distal end 114 and a side tissue receiving port 116. Alternatively, the sleeve may have a closed distal end, or the sleeve may have an open distal end with no side aperture 116. The sleeve 110 may be formed of any suitable metallic or non-metallic material. In one embodiment, the sleeve 110 is formed of biocompatible medical grade plastic.

The isotope introducer 400 shown may comprise a plunger 402, and an elongate member 408, which may be in the form of a hollow or substantially solid rod. The introducer 400 may further include a distal tissue piercing tip 410 disposed at a distal end of the member 408. In those embodiments where member 408 includes a distal piercing tip 410, it can be advantageous to have elongate member 408 be relatively stiff. By 'relatively stiff' in this context, it is meant that the tip 410 of the introducer 400 may be inserted into sleeve 110 in a generally straight line path and the tip 410 pressed or otherwise advanced into a tissue mass without breaking, buckling, or otherwise excessively deforming the introducer 400. The introducer 400 may have a latch or other structure for releasably securing the introducer to the sleeve assembly 100, either directly or indirectly.

The introducer 400 may be formed of any suitable metallic or non-metallic material, and in one embodiment may be formed of a relatively rigid medical grade, biocompatible plastic of sufficient compressive rigidity and strength to advance tip 410 into tissue. The introducer may be sized and shaped such that when the elongate member 408 is fully inserted into sleeve 110, the distal tip 410 extends through the distal opening 114 of sleeve 110, and the isotope portion 420 is generally aligned with the side tissue receiving port 116, as shown in FIG. 1A. The introducer 400 may be disposable, or may be adapted for repeated use.

The isotope portion 420 comprises one or more isotopes visible under one of PET and/or BSGI, and may additionally include other materials, such as one or more binder materials or encapsulating coatings for covering the one or more isotopes. The isotope portion 420 may comprise a liquid, a solid, a gas, or combinations thereof. The isotope portion may be disposed within the elongate member 408, such as by being molded into the member 408, or such as being disposed within a cavity within the member 408.

The sleeve 110 shown in FIGS. 1 and 1A has a side tissue receiving opening 116 disposed proximally of the distal open end 114. The opening 116 may correspond with a transverse (side) opening in a biopsy needle through which tissue is received. After the isotope portion 420 has been positioned in the sleeve 110, the sleeve with isotope 420 may be positioned with a tissue mass, and imaged using PET and/or BSGI to determine the location of the side opening 116 with respect to the tissue mass.

The introducer 400 may then be removed from the sleeve 110, and the biopsy device needle may be inserted into the sleeve such that the needle side opening is substantially aligned with the side opening 116. A hollow cutter inside the biopsy probe may then be translated and rotated within the needle to sever tissue prolapsed or otherwise received (such as by being drawn in by vacuum) through the side opening 116 in the sleeve 110 and the side opening in the biopsy device.

The isotope introducer 400 in the example of FIG. 1 is inserted in the sleeve 110. The introducer 400 described above and shown in FIG. 1 and FIG. 1A can perform as an obturator, such as while the sleeve 110 is inserted into tissue. Alternatively, a separate obturator may be provided and inserted with the sleeve into tissue, and the obturator may then be removed from the sleeve while the sleeve remains in tissue to be imaged, and the introducer 400 may be inserted into the sleeve 110, such that isotope portion 420 is substantially aligned with the side opening 116 while the sleeve is in tissue. Still further, in another embodiment the isotope introducer 400 may be insertable into an otherwise separate obturator.

To the extent that the sleeve prevents certain portions of the isotope rod from being "visible" under an imaging modality, the side opening in the sleeve may provide a window through which the isotope rod may be more easily "seen" under the imaging system in use. Such visibility may thus help indicate the location of the sleeve's side opening, which may in turn indicate the location of tissue that would be captured by a biopsy device whose needle is inserted into the sleeve after the isotope rod is withdrawn. The location and alignment of the isotope with the side opening may thus provide targeting of tissue.

In some uses, the location of target tissue may be predetermined, the sleeve may be inserted to reach the target, and the sleeve 110 and introducer 400 may be viewed under PEM and/or BSGI to confirm proper placement of the side opening 116. Alternatively, the position of the sleeve may be adjusted in real time, while viewing both a suspicious lesion and the location of the side opening 116 as indicated by the isotope rod showing through the transverse opening.

In accordance with one method of using the device in FIGS. 1 and 1A, the method may include the steps of providing a composition to the patient which identifies or otherwise tags specific tissue mass cells (e.g. cancer cells) to be visible under PET and/or BSGI imaging, imaging the breast using PET and/or BSGI, determine the location of the tissue mass of interest, inserting the isotope introducer 400 into the sleeve assembly 100 to substantially align the isotope portion 420 with the side opening 116, set a depth of insertion for the sleeve assembly (e.g. z stop) based on location of the tissue mass of interest within the breast, advance the sleeve assembly with introducer 400 into the breast, distal tip 410 first, and view or otherwise image the isotope portion 420 (and so side opening 116) with respect to the tissue mass of interest.

Figure 2:
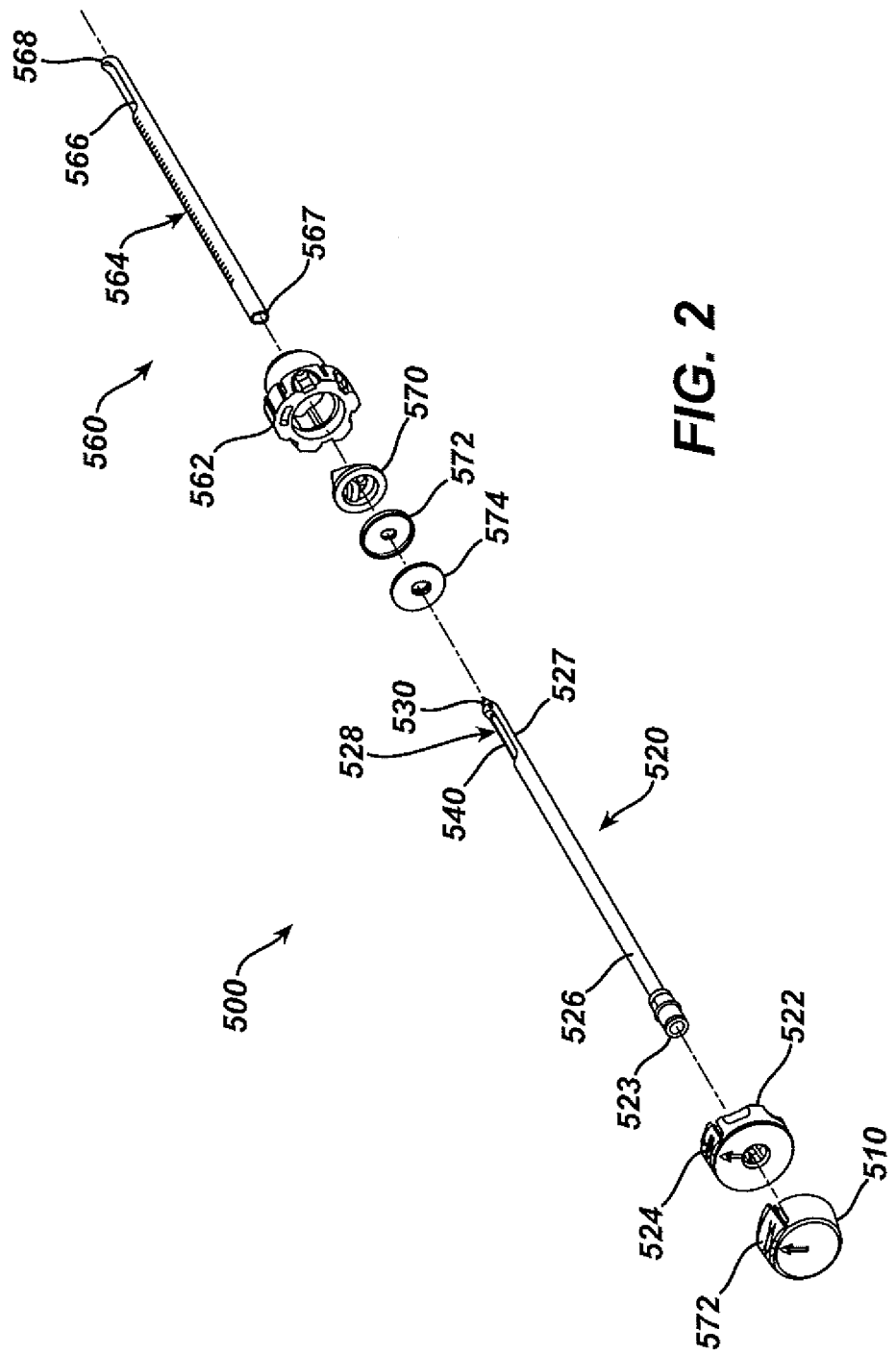
FIG. 2 depicts an exploded view of an alternative embodiment of a targeting assembly.
Figure 2A:
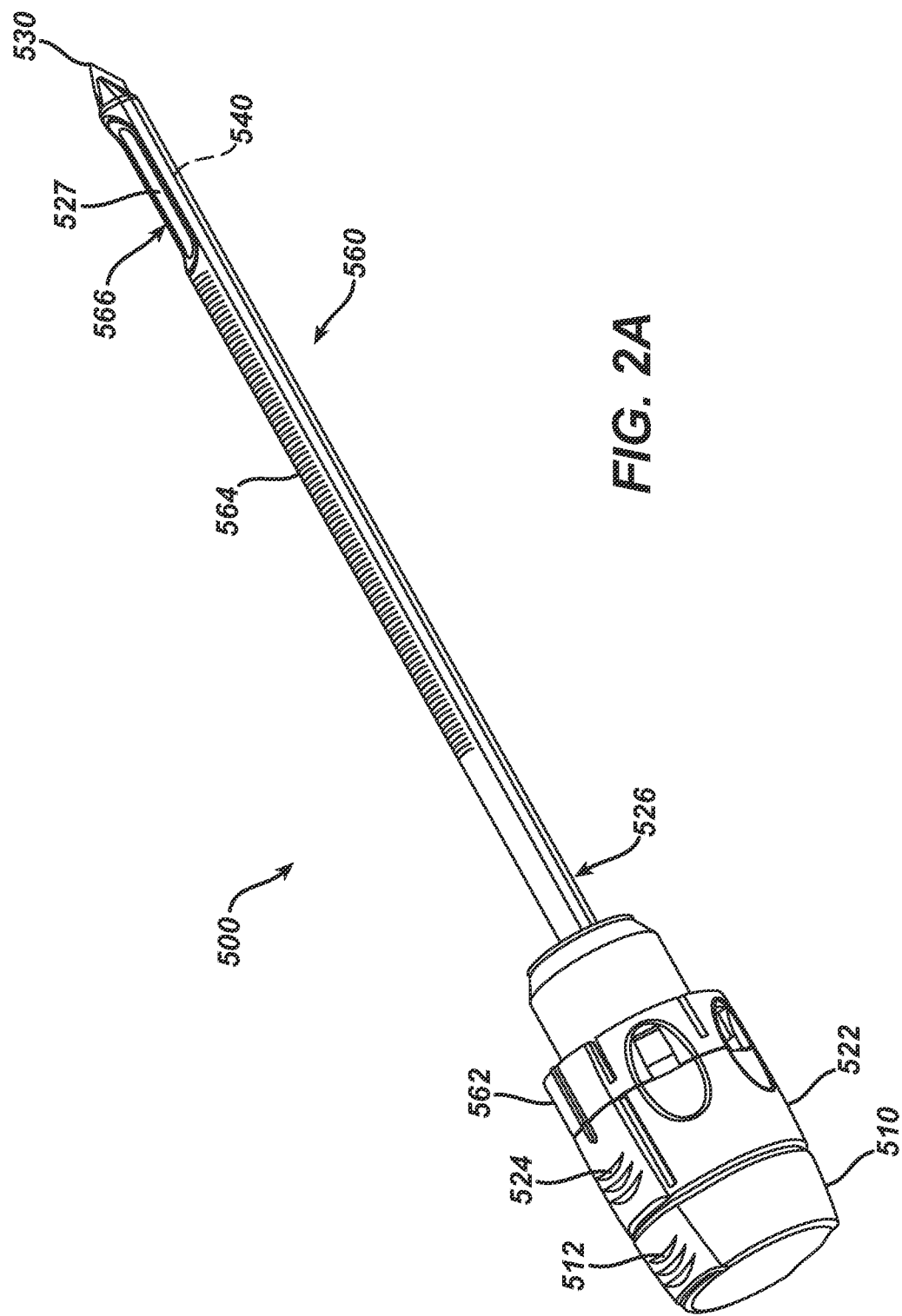
FIG. 2A depicts an isotope introducer of the target assembly of FIG. 2.
Figure 2B:
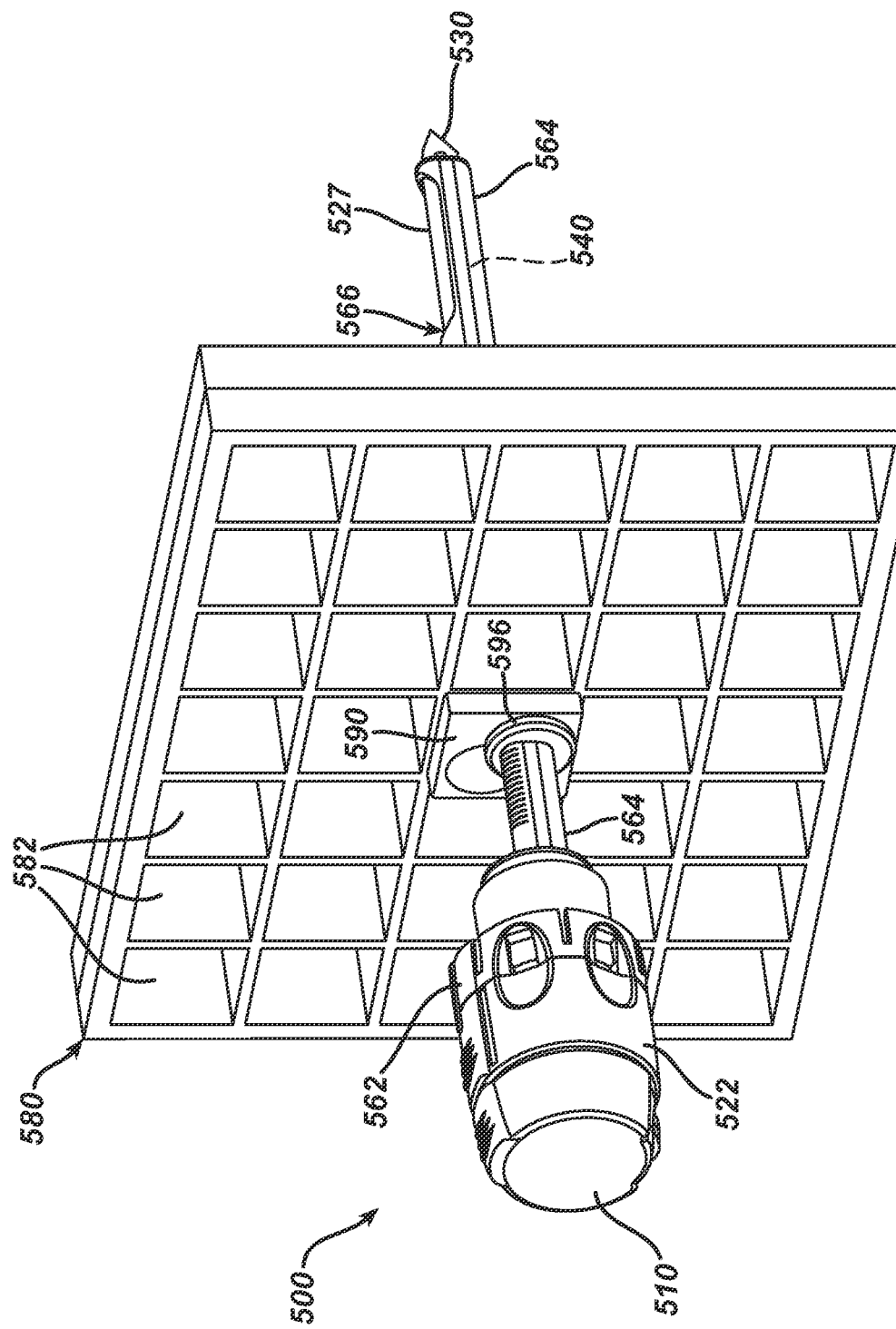
FIG. 2B depicts the target assembly of FIG. 2 positioned in guide structure inserted in one of a plurality of openings in a positioning grid, such that a proximal portion of the target assembly is disposed on one side of the grid, and such that a distal portion of the target assembly comprising an isotope portion is disposed on the other side of the grid.

FIGS. 2, 2A, and 2B illustrate another embodiment of the present invention. FIG. 2 illustrates a target assembly 500 comprising an obturator seal cap 510, an isotope introducer in the form of obturator assembly 520, and a sleeve assembly 560. Obturator seal cap 510 may have a feature 512 adapted to lock and/or locate the cap 510 with respect to an obturator hub 522 of an obturator assembly 520.

Obturator assembly 520 may include an obturator hub 522 having a feature 524 adapted to lock and/or locate the the obturator hub 522 with respect to the sleeve assembly 560. An obturator shaft 526, which may be hollow shaft, extends distally from hub 522 and may have a distal tissue piercing tip 530. The obturator shaft 526 shown includes a surface feature 528, which may be in the form of a recess, notch, or cavity, in which the isotope portion 540 may be disposed. The feature 528 as shown comprises a recess extending through a wall of the hollow shaft 526, with recess 528 disposed proximally of the tip 530, and the recess 528 may communicate with an internal lumen that extends distally from a proximal opening 523 of shaft 526. The isotope portion 540 may comprise a solid, liquid, and/or gas disposed in the recess 528, or may be a component molded or otherwise formed to fill or partially fill the recess 528.

The sleeve assembly 560 shown in FIG. 2 comprises a proximal sleeve base 562, and a sleeve 564 having a proximal end 567 and the sleeve 564 extending distally from base 562. The sleeve 564 is shown having a side opening 566 and a distal open end 568, with a lumen extending between proximal end 567 and distal open end 568. The sleeve assembly 560 may further comprise a duckbill seal 570 for providing a seal when obturator shaft 526 is removed from sleeve assembly 560, a seal 572, such as a wiper seal or lip seal for providing a seal around shaft 526 when the obturator shaft 526 is disposed within the sleeve assembly 560, and a seal retainer 574 adapted to retain seals 570 and 572 within a bore in base 562.

FIG. 2A illustrates the isotope introducer, in the form of an obturator assembly 520, with the obturator shaft 526 disposed within sleeve 564 with a bottom surface 527 of shaft 526 facing the opening 566 (surface 527 shown visible through opening 566 in FIG. 2A), such that recess 528 in the obturator shaft 526 (and the isotope portion 540) faces downward, away from the side opening 566 formed in the sidewall in the sleeve, and such that the isotope 540 is substantially aligned (longitudinally) with the opening 566.

The obturator shaft 526 may be inserted into the sleeve 564 so that the tip 530 extends from open distal end 530 of sleeve 564 and the isotope 540 faces away from opening 566. By inserting the shaft 526 into sleeve 564 such that the isotope portion 540 is substantially aligned with, but faces away from side opening 566 formed in a sidewall of sleeve 564, tissue contact with the isotope portion may be avoided, and the need for an additional sleeve or protective cover between the isotope portion 540 supported by shaft 526 and the opening 566 is avoided.

FIG. 2B illustrates the target assembly 500, with sleeve assembly 560 supported in a grid member 580 having a plurality of openings 582 therethrough. The sleeve assembly 560 extends through an opening in a guide member 590 sized and shaped to be received in one or more of the openings 582. The guide member 590 supports the isotope introducer/obturator and the sleeve assembly relative to the grid member 580. Grid member 580 may be provide a portion of a breast compression member and/or be movably supported relative to the patient's breast.

In one method of using the device shown in FIGS. 2, 2a, and 2b, the patients's breast may be imaged using PET and/or BSGI to determine the location (e.g. spacial coordinates such as x, y, z cartesion coordinates) of a target tissue lesion with respect to a reference frame. The guide member 590 may then be placed in one of the openings 582 based on the determined location (e.g. x, y coordinates) of the target tissue lesion. The obturator assembly may be positioned within the sleeve assembly such that the isotope portion 540 is substantially aligned with side opening 566 in the sleeve assembly, but with the isotope portion 540 facing downward, and substantially opposite opening 566.

A z-stop device, such as depth ring stop 596 (FIG. 2B) may be employed to set the depth of insertion (z coordinate) of the side opening 566 and/or tip 530 into the breast. As the sleeve and obturator are inserted into the breast, the user may use PET and/or BSGI to view, in real time, the targeting set being inserted to the lesion site as it is penetrating the breast.

The bottom surface 527 of obturator shaft 526 and sleeve 564, in combination, may act as a cover to prevent the isotope from coming into contact with the breast tissue (e.g., for sterility reasons). Once location is confirmed, then the obturator may be removed with the isotope, and the needle of a biopsy device may be inserted into the sleeve 564 to take tissue samples.

In other variations, the sleeve and/or obturator may include one or more isotope portions (e.g., near the distal end of the sleeve and/or obturator). Such isotope portions may be internal (e.g., impregnated, etc.) and/or external (e.g., coatings or stickers, etc.).

Figure 2C:
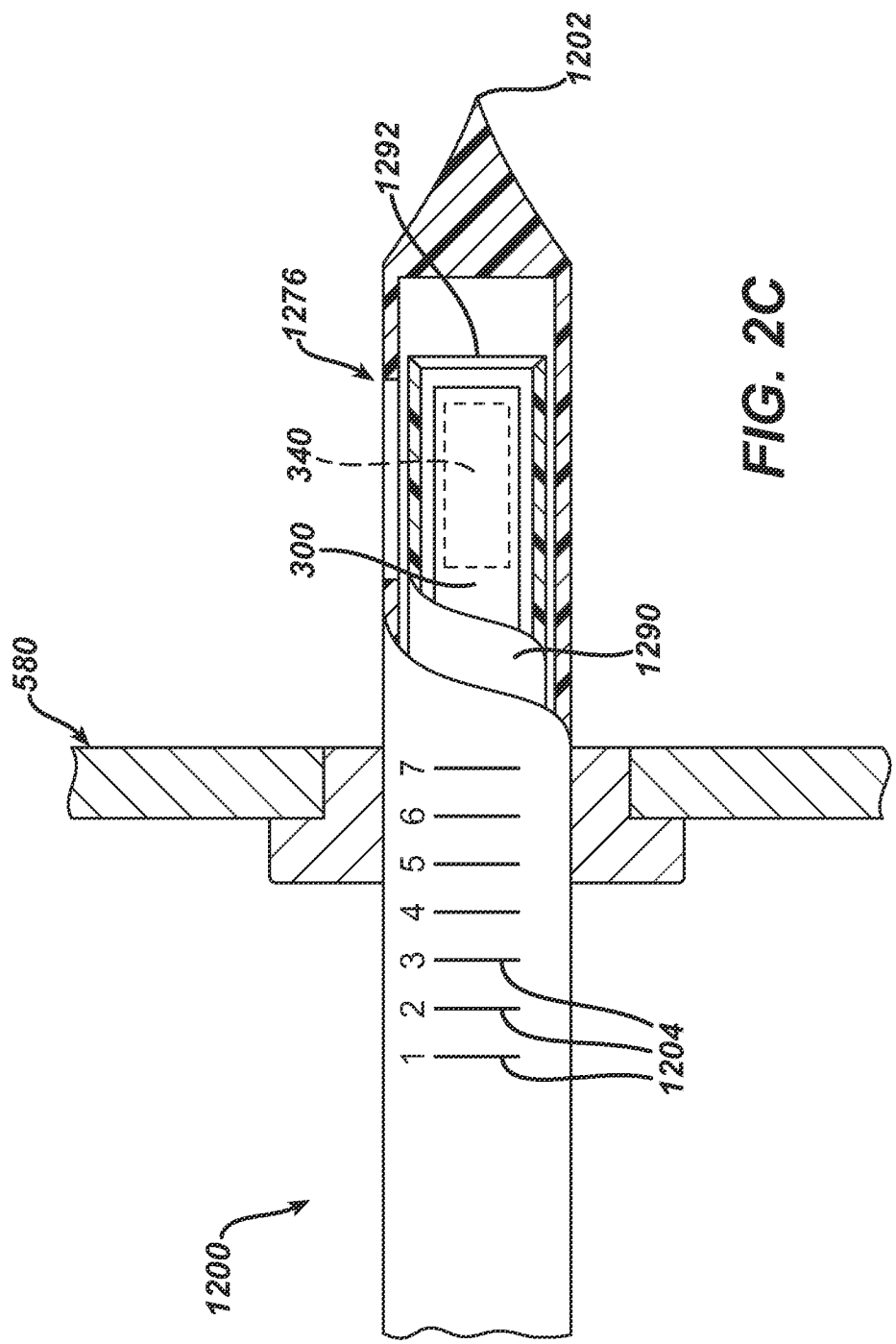
FIG. 2C depicts a biopsy needle having a side tissue receiving opening, the biopsy needle extending through a guide structure inserted in a positioning grid, with a hollow cutter advanced distally in the needle to close the side tissue receiving opening, and with an introducer carrying an isotope portion advanced distally within the cutter to position the isotope in substantial alignment with the side tissue opening in the needle.

FIG. 2C depicts another embodiment employing a grid 580. In FIG. 2C, a guide 590 is shown inserted in an opening in the grid 580. The guide has a through bore sized and shaped to receive and support a biopsy needle 1200 inserted in the bore to extend through the guide 590.

The biopsy needle 1200 shown in FIG. 2C is shown partially cut away to reveal a hollow cutter 1290 disposed within the needle 1200, and the cutter 1290 is shown partially cut away to reveal an isotope introducer 300 disposed within the hollow cutter 1290.

The needle 1200 is shown having a distal tissue piercing tip 1202 and a side tissue receiving opening 1276 disposed proximally of the tip 1202. The biopsy needle 1200 is also shown having a plurality of depth (z-direction) indicating indicia 1204 on the outer surface of the needle. The depth indicating indicia 1204 can be generally equidistantly spaced apart along the longitudinal axis of the needle, and can take any suitable form, such as for instance lines, ribs, indentations, and/or score marks. The indicia can include numerical or color coded information for placement of the needle at a desired depth (z-coordinate) within the patient's breast.

In FIG. 2C, the distal cutting edge 1292 of the cutter 1290 is shown advanced distally past the side opening 1276, so as to close the side opening 1276 from the internal lumen of the needle 1200. In one embodiment, the needle 1200 with side opening 1276 closed by cutter 1290 can be advanced through the guide 590 into the patient's breast. The isotope introducer 300 may then be advanced distally within the hollow cutter 1290 so that an isotope portion 340 associated with the distal end of the introducer 1290 is positioned in substantial alignment with the side opening 1276 of needle 1200. The introducer 300 may be in the form of a relatively flexible or relatively rigid rod sized and shaped to pass through the hollow cutter 1290. The isotope portion 340 may be disposed within the distal end of introducer 300 (as shown in phantom in FIG. 2C), or the portion 340 may be attached to the distal end of the introducer 300.

The cutter 1290 as positioned in FIG. 2C may act as a shield or otherwise separate the isotope portion from direct contact with the patient's tissue. The position of the isotope portion 340, aligned with the side opening 1276, may be imaged using PET, PEM, BSGI, and/or any other suitable nuclear imaging procedure, to verify that the opening 1276 is positioned correctly with respect to the tissue mass of interest. If desired, the position of opening 1276 may be varied with respect to the tissue of interest in real time using the image information from the selected imaging procedure. Once the opening 1276 is positioned in the desired location, the introducer and isotope portion may be withdrawn from the cutter, and the cutter may be retracted proximally to position the cutter distal end 1292 at a position proximal of the opening 1276. Vacuum may be provided through the cutter and/or a separate vacuum lumen to draw tissue into the opening 1276. The cutter may then be advanced distally to sever the tissue drawn into the opening 1276.

FIGS. 3 and 3A illustrate an isotope introducer assembly 600 according to another embodiment of the present invention, in which the assembly 600 may be used to introduce and/or position an isotope with respect to a biopsy device. The introducer assembly 600 shown in FIG. 3 includes a sleeve 610, a grip 620 disposed at or adjacent to an open proximal end 612 of the sleeve 610 (grip not shown in FIG. 3A), and an introducer component 630 comprising a plunger 632 and an elongate introducer member in the form of a rod 634. The sleeve 610 and the rod 634 can both be relatively flexible.

By "relatively flexible" in this context it is meant that the sleeve 610 and insertion rod 634 may be resiliently bent or otherwise resilient deformed through an angle of at least 60 degrees without breaking the sleeve 610 (or the member 634 within the sleeve) to permit the sleeve 610 and member 634 to be inserted along a non-linear path, such as for insertion in a biopsy device.

Figure 3B:
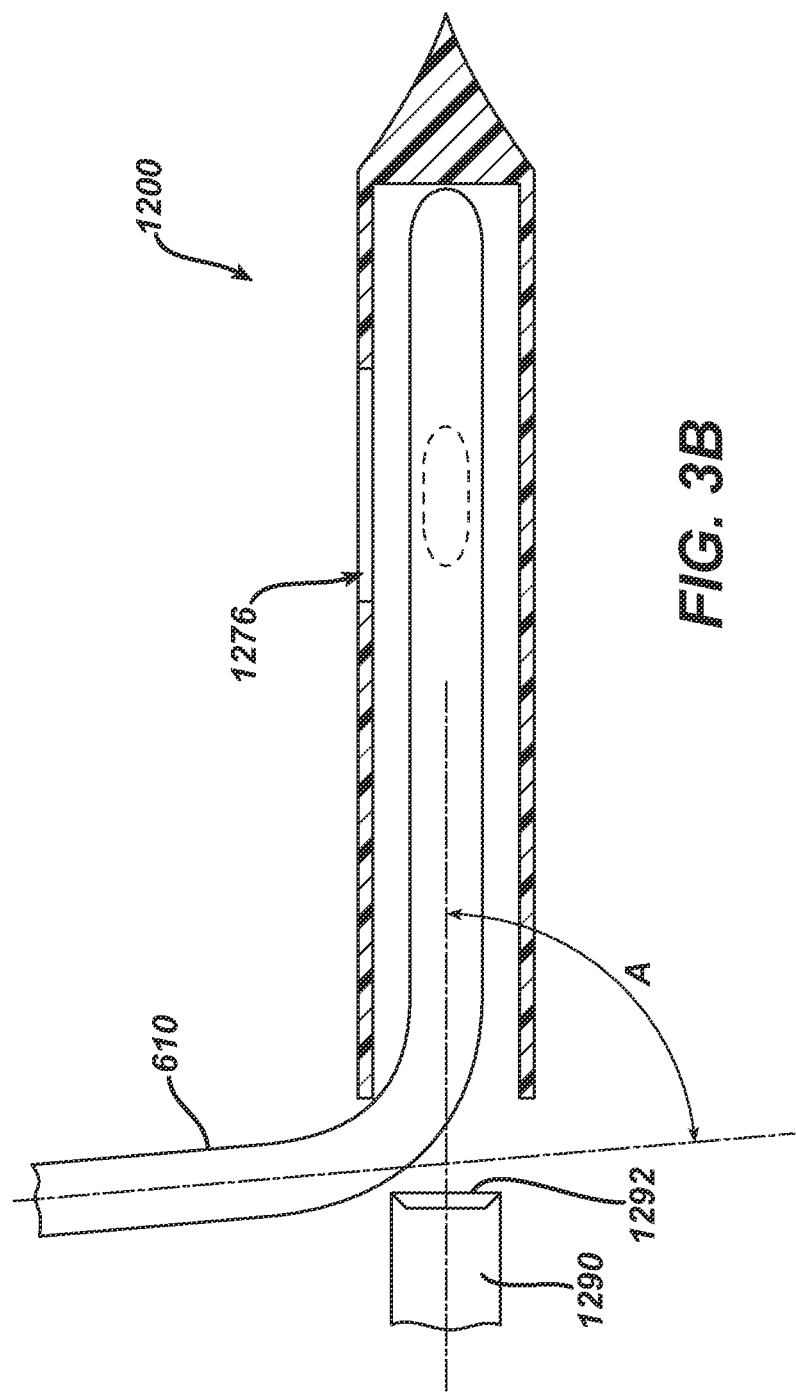
FIG. 3B illustrates the relatively flexible hollow tube deformed through an angle A, such that the flexible hollow tube may be advanced along a non-linear path into a biopsy needle to position an isotope in substantial alignment with a side opening in the biopsy needle.

FIG. 3B illustrates a sleeve 610 deformed through an angle A of between about 60 and 90 degrees, for insertion in a proximal end of a biopsy needle 1200, with a distal cutting edge 1292 of a hollow cutter 1290 retracted proximally from the proximal end of the needle 1200. In one embodiment, the sleeve and rod may be bent through an angle of at least about 135 degrees without breaking. The sleeve 610 can be in the form of a thin wall hollow tube having an open proximal end 612 and a closed distal end 614. As shown in FIG. 3A, the sleeve 610 can have an internal lumen 618 into which member 634 may be slidably inserted.

An isotope portion 640 may be operatively associated with a distal portion of member 634. For instance, in FIG. 3A the isotope portion 640 (shown in phantom) may be disposed within the member 634, such as by molding the member 634 around isotope portion 640, or otherwise encapsulating the portion 640 within the member 634. In FIG. 3A, the isotope portion 640 is disposed a predetermined distance D from the distal end of the sleeve 610 when member 634 is fully inserted into lumen 618 of sleeve 610. Alternatively, the portion 640 may be joined to a distal end of the member 634, or in yet another embodiment the isotope portion may be a separate piece that is pushed by member 634 to a desired distance D from the distal end of the sleeve 610. In yet another embodiment, the rod 634 may be eliminated, and the isotope may be attached to or otherwise disposed within the sleeve 610, such as being fixed within the hollow sleeve 610 at a predetermined distance from the end of sleeve 610.

The isotope portion 640 may contribute to the stiffness of the distal portion of the member 634. In one embodiment, the member 634 extends proximally from the portion 640 a distance at least 10 times the axial length of the portion 640, and the member 634 has a proximal portion extending intermediate the plunger 632 and the isotope portion 640, which proximal portion is more flexible than the distal portion of the member 634 associated with and encapsulating the isotope portion 640. Accordingly, in those cases where the portion 640 is a relatively short, stiff, relatively stiff component, the relatively more flexible proximal portion of the introducer member 634 permits the portion 640 to be advanced along a non-linear path to a desire location.

When the sleeve 610 is inserted into a biopsy device, such as a biopsy needle, the position of the isotope portion 640 relative to a feature of the biopsy needle, such as a side tissue receiving aperture, may be established based on various dimensions, such as for instance the length of the biopsy needle and the distance D. The isotope may be positioned in the distal portion of the sleeve 610 so that the isotope is aligned with the side tissue receiving opening (in either a target set sleeve or the biopsy needle) when the sleeve 610 is fully advanced within the biopsy device. Using PET, PEM, BSGI, or other suitable nuclear imaging methods, the position of the isotope (and so the side tissue receiving opening) can be confirmed with respect to the lesion of interest.

If desired, a kit of introducers may be provided, wherein at least some of the introducers 600 have a different characteristic dimension D and/or at least some of the introducers have sleeves 610 and/or introducer members with different lengths. A kit may also be provided with one or more sleeves 610, and a plurality of members 634, each member 634 insertable in at least one sleeve, where one or more of the members 634 have the isotope portion 640 disposed at a different positions along the length of the member 634. The members 634 and isotope portions 640 may be disposable or reusable. The distance D can be provided such that the isotope is aligned with the side tissue receiving opening in either a biopsy device and/or a target sleeve.

In one alternative, the sleeve 610 may also include a side aperture. The member 634 may be inserted into sleeve 610, to position isotope portion 640 for imaging. The member 634 may then be removed, and one or more biopsy markers may be directed through sleeve to be deployed through the side opening in the sleeve. The biopsy markers may be directed through the sleeve alone, or the markers may delivered through the sleeve with a tubular marker applier.

In another embodiment, the sleeve 610 may have a side opening, and the sleeve may be size to receive a biopsy needle such that a side tissue opening of the biopsy needle is aligned with the side opening of the sleeve 610. After the isotope portion 640 has been imaged with the side opening of the sleeve 610 to confirm the side opening is in a desired location, the member 634 may be removed from the sleeve 610, and the biopsy needle may be advanced into the sleeve 610. A cutter may be advanced through the biopsy needle to cut tissue received through the aligned side openings in the sleeve and biopsy needle. The biopsy needle may then be removed, and one or ore markers may delivered through the sleeve. Alternatively, the biopsy needle may remain in place in the sleeve, the cutter may be retracted, and the markers may be delivered through the biopsy needle to the aligned side openings in the sleeve 610 and the biopsy needle.

In another embodiment, the isotope may be positionable at a plurality of predetermined locations along the length of the sleeve 610. For instance, the member 634 could include external ribs or ridges spaced along the length of the member 634. As the member 634 is advanced or withdrawn from sleeve 610, the ribs or ridges, when aligned with the proximal end 612 of the sleeve, would correspond to different predetermined distances D. Alternatively, the member 634 may have indicia, such as color coded lines, numerical indicators, or lines of various configuration and/or width, and/or other indicators along the length of the member 634 to indicate predetermined positions to which member 634 may be inserted or withdrawn within the sleeve 610 to provide different distances D.

For instance, in FIG. 3A two indicia are shown in the form of a relatively thin line 636A and a relatively thick line 636B extending around the member 634. As the member 634 is advanced or withdrawn from sleeve 610, the position of each indicia 636A/636B at the end 612 of the sleeve 610 correspond to two different predetermined distances D of the isotope 640 with respect to tip 614.

FIG. 4 illustrates an isotope introducer device 700 comprising an isotope introducer comprising a grip 710 and an elongate member 720 having an isotope portion operatively associated with a distal end of the member 720. The isotope portion 740 may be joined to the distal end of member 720 using any suitable joining method, including by adhesive bonding, molding, or with a fastener. Alternatively, the portion 740 may be spaced from the distal end of member 720 by a predetermined distance. The member 720 can comprise a relatively flexible rod or tube formed of a medical grade, biocompatible plastic. The introducer in FIG. 4 provides a one piece device for introducing an imageable isotope to a desired location with in a biopsy device, without requiring a plunger.

As yet another variation, an introducer device may include kit including one or more flexible members 720, of the type shown in FIG. 4, and a plurality of tips that can be releasably joined to a distal portion of the member 720. The kit may include tips of various lengths, diameters, and/or isotope compositions. In yet another embodiment, the isotope may be provided as a sticker or decal which may be affixed to a portion of the flexible member 720.

Figure 5:
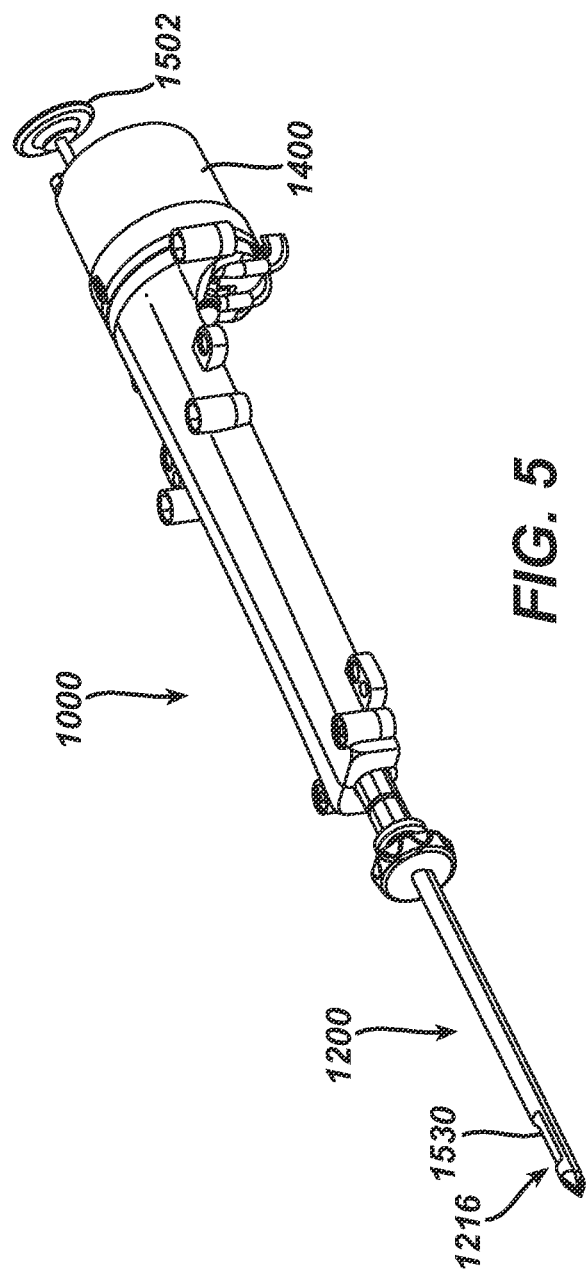
FIG. 5 depicts a perspective view of an introducer comprising an isotope portion extending through a biopsy device, such that a proximal end of the introducer extends proximally from the proximal end of the biopsy device, and a distal end of the introducer associated with an isotope portion is disposed within an outer needle of the biopsy device.

FIG. 5 illustrates a generalized biopsy device 1000 comprising a housing 1100, a biopsy needle 1200 extending distally from the housing, and a tissue sample container 1400 disposed at a proximal end of the housing 1100. The biopsy needle 1200 is shown having a side tissue receiving aperture 1216 and a distal piercing tip. An isotope introducer, such as one of the introducer device having one or more of the components shown in FIGS. 1-4 is shown inserted into the proximal end of the biopsy device 1000, such as a proximal opening in the tissue sample compartment 1400 communicating with a hollow cutter of the biopsy device.

In FIG. 5, the introducer is provided with sufficient length to extend substantially the full length of the biopsy device 1000, from a plunger 1502 disposed proximal of the compartment 1400, to a distal portion of the introducer labeled 1530, shown aligned with and visible through the side tissue receiving opening in FIG. 5. The distal portion 1530 may carry or enclose an isotope portion, or alternatively the distal portion 1530 may be the isotope portion.

In those embodiments where the biopsy device includes a hollow internal cutter which translates and rotates within the biopsy needle 1200, the isotope introducer and isotope portion may be sized and shaped to pass through the hollow internal cutter. The biopsy device may include a proximal opening communicating with hollow lumen of the internal cutter. The cutter may be advanced distally to close the side opening in the needle, such that the distal portion of the cutter is disposed in the distal portion of the needle 1200.

The isotope portion can then be advanced through the hollow cutter such that the isotope is aligned with the side opening in the needle, but spaced from the side opening in the needle by the cutter. Such an arrangement has the advantage that the cutter prevents direct contact between the isotope portion and the tissue adjacent the side opening in the biopsy needle. FIG. 5A illustrates a hollow cutter 1290 having an open distal cutting edge 1292 advanced distally within biopsy needle 1200 beyond the distal end of side opening 1276, so that the upper side wall of the cutter closes the side opening 1276. FIG. 5A also illustrates the isotope portion 1530 advanced into the hollow cutter and aligned within the cutter with the side opening 1276. Once the isotope is imaged to confirm the location of the side opening 1276, the isotope may be withdrawn proximally through the cutter, the cutter may be retracted proximally to open the side opening 1276, tissue may be drawn (e.g. by vacuum) into the opening 1276, and the cutter may be advanced distally to sever the tissue with cutting edge 1292. Alternatively, the cutter may be retracted proximally of the biopsy needle side opening, and the isotope may be advanced through the biopsy needle. And substantially aligned with the side tissue receiving opening in the biopsy needle 1200.

The isotope may be positioned in the biopsy needle 1200 prior to the insertion of the needle 1200 into the breast. Generally, it is desirable to have the side tissue opening 1276 closed or at least substantially closed when the needle 1200 is inserted in the breast. The opening 1276 may be closed by advancing the cutter to close the opening 1276, or alternatively, the isotope portion and introducer member may be advanced through the cutter to close off the opening 1276 (where the isotope portion and introducer member are sized and shaped to fit down the inside of the hollow inner cutter), or the hollow internal cutter may be retracted, and the isotope portion and introducer can be advanced to close off the opening 1276. For instance, in FIG. 5, a distal portion 1530 of the isotope introducer is shown closing off the opening 1276. The needle 1200 with isotope disposed within the needle can be imaged, such as by using PET or BSGI. Then, the isotope and introducer can be removed from the needle 1200, and the inner hollow cutter can be advanced to sever tissue received in the opening 1276.

In some variations, a movable sleeve or other component is provided about needle 1200, permitting at least a portion the isotope rod to be covered, such as to prevent the rod from touching tissue through the transverse opening. Alternatively, a cutter within the needle may provide at least some degree of cover for the isotope rod, as disclosed above. A member may be used to introduce (e.g. by carrying or pushing) the isotope, with the member configured to fit within the inner diameter of a hollow tubular cutter disposed within the outer needle. The cutter may be advanced distally (e.g., to "close off" the transverse opening) as the needle is inserted into tissue, and the cutter may be retracted at least partially to "reveal" the isotope rod when the needle is disposed in tissue.

FIG. 6A and FIG. 6B show a modification that may be provided in a biopsy needle to provide imaging of a tissue receiving opening under PET and/or BSGI. FIG. 6A is a top view of a needle 1400, and FIG. 6B is a schematic cross-section taken along lines 6-6 in FIG. 6A.

The biopsy needle 1400 of FIGS. 6A and 6B has a tissue piercing closed tip 1423, a side (transverse) opening 1416, and a perforated vacuum wall 1434 disposed below the opening 1416. Vacuum wall 1434 has a plurality of openings 1436 there through for communicating vacuum provided through a vacuum passageway 1438. The vacuum passageway 1438 is disposed below an inner hollow cutter 1600. Cutter 1600 has an open distal cutting end 1610, and cutter 1600 is translatable and rotatable within a cutter lumen of needle 1400.

As shown in the Figures, an isotope imageable under PET and/or BSGI may be disposed on the vacuum wall 1434. Accordingly, the opening 1416 will be relatively more visible under PET and/or BSGI. While the wall 1434 is shown as extending only part of the length of the needle in this example, other variations may have a wall extending the full length of the needle.

For instance, the wall 1434 may be coated or impregnated with an isotope. Accordingly, when the wall is "revealed" through the transverse opening of the needle, such as when cutter 1600 is retracted proximally, the wall may be seen via PEM and/or BSGI imaging. Being on or in the wall, within the needle, may prevent the isotope from coming into direct contact with tissue (e.g., tissue that is not being severed by the cutter). In some applications, the isotope may be imageable via PEM and/or BSGI, even with the cutter translated distally (e.g., the wall can be "seen" through the cutter using the imaging technique).

Figure 7:
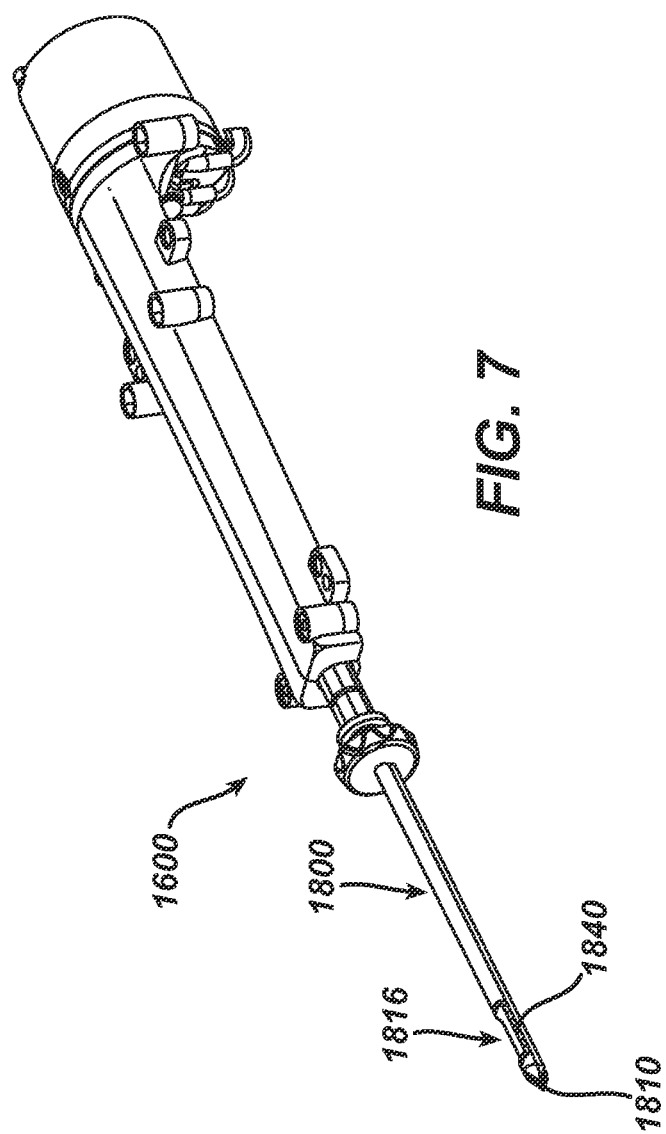
FIG. 7 depicts a biopsy device incorporating an isotope disposed around at least a portion of a side tissue receiving opening in the biopsy needle.

FIG. 7 illustrates a biopsy device 1600 comprising a biopsy needle 1800 having a distal piercing tip 1810 and a side opening 1800. In the embodiment of FIG. 7, an isotope visible under PEM and/or BSGI is associated with at least a portion of the perimeter of the opening 1816. In FIG. 7, the isotope is shown in the form of a decal 1840 that substantially surrounds the opening 1816, to provide imaging of the perimeter of the opening 1816 under PET and/or BSGI.

The decal comprising the isotope may be applied to the needle just before the biopsy procedure, as opposed to when the needle is manufactured. After the biopsy procedure is complete, the sticker may be removed from the needle and disposed of properly. The decal 1840 may comprise a first outer layer, such as a coating or film layer substantially impervious to moisture, and a second inner layer comprising the isotope used in imaging. The outer layer can be employed to prevent contact of the isotope with the tissue. Alternatively, the perimeter of the side opening may be impregnated with the isotope, or the isotope may be provided as a coating about the perimeter of the opening.

While the isotope sticker of the present example is shown in FIG. 7 as extending about the full perimeter of the transverse opening, it will be appreciated an isotope sticker (or other type of isotope marking) need not extend about the full perimeter of a transverse opening. For instance, in some versions, only the distal and proximal edges are marked. In any case, it will be appreciated that the isotope sticker of the present example may make the transverse opening of the probe needle stand out under PEM and/or BSGI imaging, which may facilitate real time targeting and/or for confirmation of proper needle location as described above.

Figure 8:
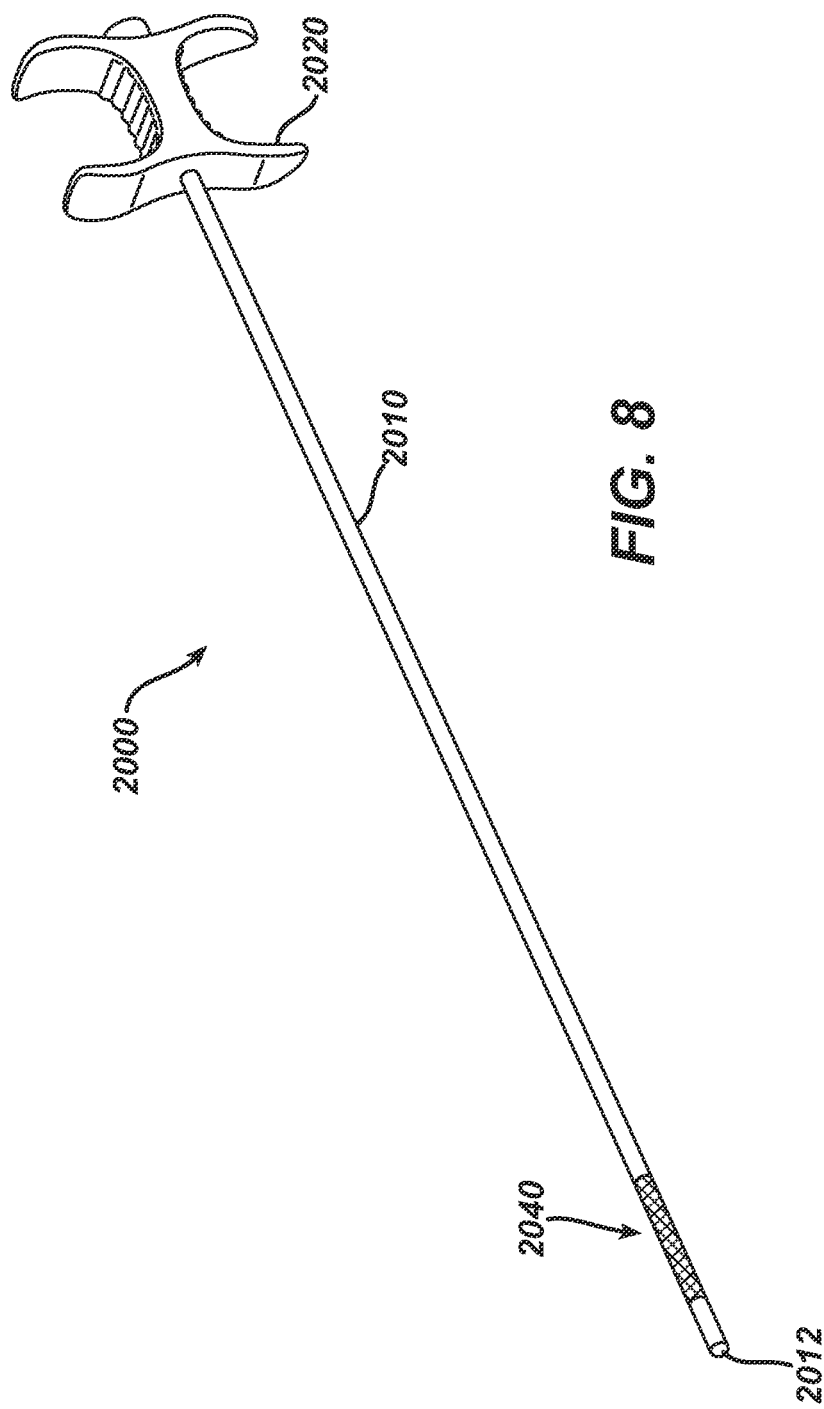
FIG. 8 depicts a perspective view of an introducer having an elongate member in the form of a rod, the rod having an isotope in the form of a coating or decal positioned on the rod in spaced relationship from the distal end of the rod.

FIG. 8 depicts a perspective view of an isotope introducer device 2000 comprising a grip 2020 and an elongate member 2010 extending distally from the grip. The elongate member may be a flexible rod or tube, or alternatively, the elongate member 2010 may be in the form of a relatively rigid rod or tube. An isotope portion 2040 may be disposed on an outer surface of the member 2010, such as in a predetermined spaced relation from the distal end 2012 of member 2010. The isotope portion 2040 may be in the form of a releasable decal or coating applied to the member 2010. After the biopsy procedure is complete, the sticker may be removed from the member 2010 and disposed of properly.

In one embodiment, a kit may be provided having one or more introducer devices 2000. The devices 2000 can be provided with elongate members having different lengths and/or isotope portions disposed at different positions relative to the distal ends of the devices. The isotope carrying decals may be provided in the kit, or separately, such that the position of the isotope on the elongate member can be selected at the time of use. The decals can be provided in different lengths and/or widths to accommodate different sizes of isotope introducers and/or biopsy devices.

While certain specific isotopes have been mentioned herein, it will be appreciated that any other suitable isotope may be used, as well as any suitable combinations of isotopes. Such alternative isotopes may provide emission of positrons, gamma radiation, or any other suitable type of emission or radiation. Furthermore, while PEM and BSGI are described in many of the examples herein as exemplary imaging modalities, it will be appreciated that any other suitable imaging modalities may be used, including combinations thereof. In other words, devices disclosed herein may be used in a variety of settings, including those in which some imaging modality or modalities other than PEM and BSGI are used, including but not limited to MRI, x-ray, modalities detecting radiation emitted from a patient, etc. Suitable alternative imaging modalities will be apparent to those of ordinary skill in the art in view of the teachings herein. To the extent that alternative imaging modalities are used, the devices described herein may be used with such alternative imaging modalities with or without further modifications to the devices described herein. Suitable modifications to the devices described herein, for use with PEM or BSGI imaging or any other imaging modalities, will be apparent to those of ordinary skill in the art in view of the teachings herein.

Embodiments of the present invention may have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed:

1. A biopsy apparatus comprising:
    a hollow, relatively flexible tube having an open proximal end and a closed distal end, wherein the tube comprises a completely solid wall extending between the open proximal end and the closed distal end;
    an elongate member advanceable in the tube and having a distal end, wherein the elongate member comprises at least one indicia positioned along a length of the elongate member; and
    at least one isotope disposed within the tube, wherein the isotope is positioned proximal to the closed distal end of the tube, such that a portion of the tube extends distally between the isotope and the closed distal end of the tube, and wherein the isotope is coupled to the elongate member at a position proximal to the distal end of the elongate member;
    wherein the indicia of the elongate member is configured to align with the proximal end of the tube to position the isotope at a predetermined position along a length of the tube.

2. The biopsy apparatus of claim 1 wherein the isotope is disposed at a predetermined distance from the distal end of the tube.

3. The biopsy apparatus of claim 1 wherein the isotope is enclosed within a portion of the elongate member.

4. The biopsy apparatus of claim 1 wherein the tube is non-metallic.

5. The biopsy apparatus of claim 1 comprising a Technicium Isotope T-99.

6. The biopsy apparatus of claim 1 comprising fluorodeoxyglucose.

7. The biopsy apparatus of claim 1 wherein the isotope is positionable at a plurality of predetermined locations along the length of the tube.

8. A biopsy apparatus comprising:
    a biopsy needle having a side aperture;
    a hollow, relatively flexible continuous tube having an open proximal end and a closed distal end;
    a flexible elongate member advanceable in the tube and having a distal end; and
    at least one isotope disposed within the tube, wherein the isotope is coupled to the elongate member at a position proximal to the distal end of the elongate member, wherein the elongate member comprises a proximal portion proximal of the isotope, wherein the elongate member comprises a distal portion distal of the isotope;
    wherein the tube is slidably disposed in the biopsy needle, wherein the isotope is positionable adjacent to the side aperture of the biopsy needle;
    wherein the tube and the elongate member are relatively flexible, wherein the proximal portion of the elongate member is more flexible than the distal portion of the elongate member.

9. The biopsy apparatus of claim 8, wherein a portion of the elongate member protrudes proximally from the open proximal end of the tube.

10. The biopsy apparatus of claim 8, wherein the isotope is fixed to the elongate member.

11. The biopsy apparatus of claim 8, wherein the biopsy needle has a closed distal end configured to penetrate tissue.

12. The biopsy apparatus of claim 8, wherein the tube has a first length, wherein the elongate member has a second length, wherein the second length is sized such that a proximal portion of the elongate member protrudes proximally from the open proximal end of the tube when the elongate member is fully inserted in the tube.

* * * * *